United States Patent
Wu

(10) Patent No.: US 10,918,465 B2
(45) Date of Patent: Feb. 16, 2021

(54) THREE-DIMENSIONAL OBJECT SCANNING DEVICE USING STRUCTURED LIGHTS AND METHOD FOR SCANNING THREE-DIMENSIONAL OBJECT USING STRUCTURED LIGHTS

(71) Applicant: QISDA CORPORATION, Taoyuan (TW)

(72) Inventor: Po-Fu Wu, New Taipei (TW)

(73) Assignee: Qisda Corporation, Taoyuan (TW)

( * ) Notice: Subject to any disclaimer, the term of this patent is extended or adjusted under 35 U.S.C. 154(b) by 78 days.

(21) Appl. No.: 16/248,791

(22) Filed: Jan. 16, 2019

(65) Prior Publication Data
US 2019/0247157 A1     Aug. 15, 2019

(30) Foreign Application Priority Data
Feb. 12, 2018 (CN) .................. 201810144911.X

(51) Int. Cl.
| | |
|---|---|
| *A61C 9/00* | (2006.01) |
| *G06T 7/521* | (2017.01) |
| *A61B 1/24* | (2006.01) |
| *A61B 1/06* | (2006.01) |
| *A61B 5/00* | (2006.01) |

(Continued)

(52) U.S. Cl.
CPC .......... *A61C 9/006* (2013.01); *A61B 1/00172* (2013.01); *A61B 1/063* (2013.01); *A61B 1/0638* (2013.01); *A61B 1/24* (2013.01); *A61B 5/0062* (2013.01); *A61B 5/0088* (2013.01); *G06T 7/521* (2017.01); *G06T 17/00* (2013.01); *G06T 2200/08* (2013.01);

(Continued)

(58) Field of Classification Search
CPC ..... G01B 11/2509; A61C 9/006; G06T 7/521; G06T 17/00; G06T 2200/08; G06T 2207/10024; G06T 2207/10028; G06T 2207/30036; G06T 2210/41; A61B 1/0072; A61B 1/063; A61B 1/0638; A61B 1/24; A61B 5/0062; A61B 5/0088
USPC .......................................................... 375/66
See application file for complete search history.

(56) References Cited

U.S. PATENT DOCUMENTS

| | | | | |
|---|---|---|---|---|
| 6,636,629 | B1 * | 10/2003 | Sasai ..................... | G06T 3/4015 348/273 |
| 2005/0043837 | A1 * | 2/2005 | Rubbert ............... | A61C 9/0046 700/98 |

(Continued)

FOREIGN PATENT DOCUMENTS

| | | |
|---|---|---|
| CN | 101833775 A | 9/2010 |
| CN | 107257992 A | 10/2017 |

*Primary Examiner* — Joseph G Ustaris
*Assistant Examiner* — Jimmy S Lee

(57) ABSTRACT

The invention provides a three-dimensional object scanning device using structured lights and method using the same. A combination of specific monochrome light sources is used to construct the content of the structured lights to form a predetermined image, which is projected to the three-dimensional object such as an intraoral object. The combination of blue and green lights effectively eliminates reflective interference of the red or white environment within the intraoral space. Default patterns of the predetermined image are distinguished from one another by using well designed arrangement of color blocks so that specific coding information of location may be embedded and exploited.

9 Claims, 5 Drawing Sheets

(51) Int. Cl.
  *G06T 17/00* (2006.01)
  *A61B 1/00* (2006.01)
(52) U.S. Cl.
  CPC .............. *G06T 2207/10024* (2013.01); *G06T 2207/10028* (2013.01); *G06T 2207/30036* (2013.01); *G06T 2210/41* (2013.01)

(56) References Cited

U.S. PATENT DOCUMENTS

| | | | |
|---|---|---|---|
| 2015/0254819 A1* | 9/2015 | Hara | G06T 5/006 345/647 |
| 2018/0025529 A1* | 1/2018 | Wu | A61B 5/1077 345/426 |
| 2018/0328570 A1* | 11/2018 | Xi | G09G 3/003 |
| 2018/0364534 A1* | 12/2018 | Du | H01L 27/124 |
| 2019/0073753 A1* | 3/2019 | Yamauchi | H04N 9/3188 |

* cited by examiner

THREE-DIMENSIONAL OBJECT SCANNING DEVICE USING STRUCTURED LIGHTS AND METHOD FOR SCANNING THREE-DIMENSIONAL OBJECT USING STRUCTURED LIGHTS

BACKGROUND OF THE INVENTION

1. Field of the Invention

The invention relates to a scanning device and a scanning method and, more particularly, to a three-dimensional object scanning device and method using structured lights.

2. Description of the Prior Art

A conventional intraoral scanner uses structured lights to scan one single tooth or all teeth in an oral cavity. The principle of using structured lights for intraoral scan is performed by projecting a known pattern to an object in the oral cavity by a projection device of the scanner and then capturing a distorted pattern on the object by a lens of the scanner. Afterward, a back-end software performs comparison and calculation for the known pattern and the distorted pattern, so as to obtain three-dimensional size and shape of the object and construct a three-dimensional model of the object accordingly.

Due to specific conditions for intraoral scan, the structured lights may be destroyed or scattered easily by high reflective substances (e.g. blood, enamel, ceramic, metal, etc.) and environmental light entering the oral cavity. Consequently, there may be an error or broken area existing in the image. To solve the aforesaid problem, the prior art sprays tiny powders in the oral cavity to eliminate the reflective issue before scanning the oral cavity. However, the aforesaid manner will consume lots of powders and increase additional operation time and manpower. Furthermore, the conventional intraoral scanner has some disadvantages of big size, high power consumption, too much heat generated, high cost, slow image capturing rate, and so on. Moreover, in order to speed up image recognition, the prior art need to apply spatial coding to the structured light pattern. If more colors or a gradation of color is applied to the structured light pattern, it may increase the difficulty in image recognition.

SUMMARY OF THE INVENTION

Therefore, the invention provides a three-dimensional object scanning device and method to solve the aforesaid problems.

According to an embodiment of the invention, a three-dimensional object scanning device comprises a projection unit and an image capturing unit. The projection unit comprises a first monochrome light source and a second monochrome light source. The projection unit is configured to project a predetermined image to a three-dimensional object, so as to form a constructed image on a surface of the three-dimensional object. The predetermined image comprises a plurality of default patterns. Each of the default patterns comprises a first group of color blocks and a second group of color blocks. The first group of color blocks comprises at most two different color blocks. The second group of color blocks comprises at least two and at most four different color blocks. The image capturing unit is configured to capture the constructed image formed on the surface of the three-dimensional object.

According to another embodiment of the invention, the default patterns are arranged side by side to form the predetermined image, such that the first groups of color blocks and the second groups of color blocks of the default patterns are interlaced with each other to construct the predetermined image with striped pattern.

According to another embodiment of the invention, the first group of color blocks comprises black blocks and the second group of color blocks comprises blue blocks, green blocks, cyan blocks, and black blocks, wherein the blue blocks are generated by projection of the first monochrome light source, the green blocks are generated by projection of the second monochrome light source, and the cyan blocks are generated by projection of both of the first monochrome light source and the second monochrome light source.

According to another embodiment of the invention, each second group of color blocks is formed by arranging at least two and at most four different color blocks in a manner different from other second groups of color blocks.

According to another embodiment of the invention, the default patterns are square patterns and each of which comprises n*n color blocks, the n*n color blocks are arranged in a checkerboard manner to form the predetermined image, wherein n is a positive integer larger than or equal to 5.

According to another embodiment of the invention, the first group of color blocks of each default pattern comprises 3*3 color blocks in a center of the default pattern and the second group of color blocks comprises a plurality of color blocks surrounding the first group of color blocks.

According to another embodiment of the invention, the first group of color blocks of each default pattern has a first pattern type and a second pattern type, four edge blocks of the first pattern type are black blocks, and four corner blocks of the second pattern type are black blocks.

According to another embodiment of the invention, other non-black blocks in the first group of color blocks with the first pattern type are blue blocks, green blocks, or cyan blocks and have identical color, other non-black blocks in the first group of color blocks with the second pattern type are blue blocks, green blocks, or cyan blocks and have identical color, wherein the blue blocks are generated by projection of the first monochrome light source, the green blocks are generated by projection of the second monochrome light source, and the cyan blocks are generated by projection of both of the first monochrome light source and the second monochrome light source.

According to another embodiment of the invention, each second group of color blocks is formed by arranging at least two and at most four different color blocks in a manner different from other second groups of color blocks and surrounding the first group of color blocks.

According to another embodiment of the invention, the first monochrome light source is a blue light source, the second monochrome light source is a green light source, and the projection unit only comprises the blue light source and the green light source.

According to another embodiment of the invention, the three-dimensional object scanning device further comprises a back-end processing unit configured to construct a three-dimensional model of the three-dimensional object according to the constructed image and the predetermined image.

According to another embodiment of the invention, the three-dimensional object is a tooth and the three-dimensional object scanning device is an intraoral scanner.

According to another embodiment of the invention, a method for scanning a three-dimensional object using structured lights is provided. A three-dimensional object scanning device comprises a projection unit and an image capturing unit. The projection unit comprises a first monochrome light source and a second monochrome light source. The method comprises steps of the projection unit projecting a predetermined image to a three-dimensional object, so as to form a constructed image on a surface of the three-dimensional object, the predetermined image comprising a plurality of default patterns, each of the default patterns comprising a first group of color blocks and a second group of color blocks, the first group of color blocks comprising at most two different color blocks, the second group of color blocks comprising at least two and at most four different color blocks; and the image capturing unit capturing the constructed image formed on the surface of the three-dimensional object.

According to another embodiment of the invention, the method comprises step of using the projection unit to construct the default patterns of the predetermined image provided by the aforesaid embodiments. The method further comprises step of using a back-end processing unit of the three-dimensional object scanning device to construct a three-dimensional model of the three-dimensional object according to the constructed image and the predetermined image According to the three-dimensional object scanning device and the method for scanning the three-dimensional object using structured lights of the invention, the combination of blue light source and green light source are used to scan a specific three-dimensional object, such that the invention can enhance color recognition and reduce interference of white and/or red light from the three-dimensional object. Since the projection unit only uses blue light source and green light source, the invention can reduce the size of optical engine, reduce the power consumption and heat during projection, and reduce the manufacture cost for the scanning device. Furthermore, since the invention uses limited amount of color lights to perform scan, the scanning time can be reduced and the image capturing rate can be enhanced. Moreover, the structured light pattern of the invention may include spatial coding, so as to position the corresponding location rapidly.

These and other objectives of the present invention will no doubt become obvious to those of ordinary skill in the art after reading the following detailed description of the preferred embodiment that is illustrated in the various figures and drawings.

DETAILED DESCRIPTION

Certain terms are used throughout the following description and claims to refer to particular components. As one skilled in the art will appreciate, manufacturers may refer to a component by different names. In the following discussion and in the claims, the terms "include" and "comprise" are used in an open-ended fashion. Also, the term "couple" is intended to mean either an indirect or direct electrical/mechanical connection. Thus, if a first device is coupled to a second device, that connection may be through a direct electrical/mechanical connection, or through an indirect electrical/mechanical connection via other devices and connections.

Figure 1:
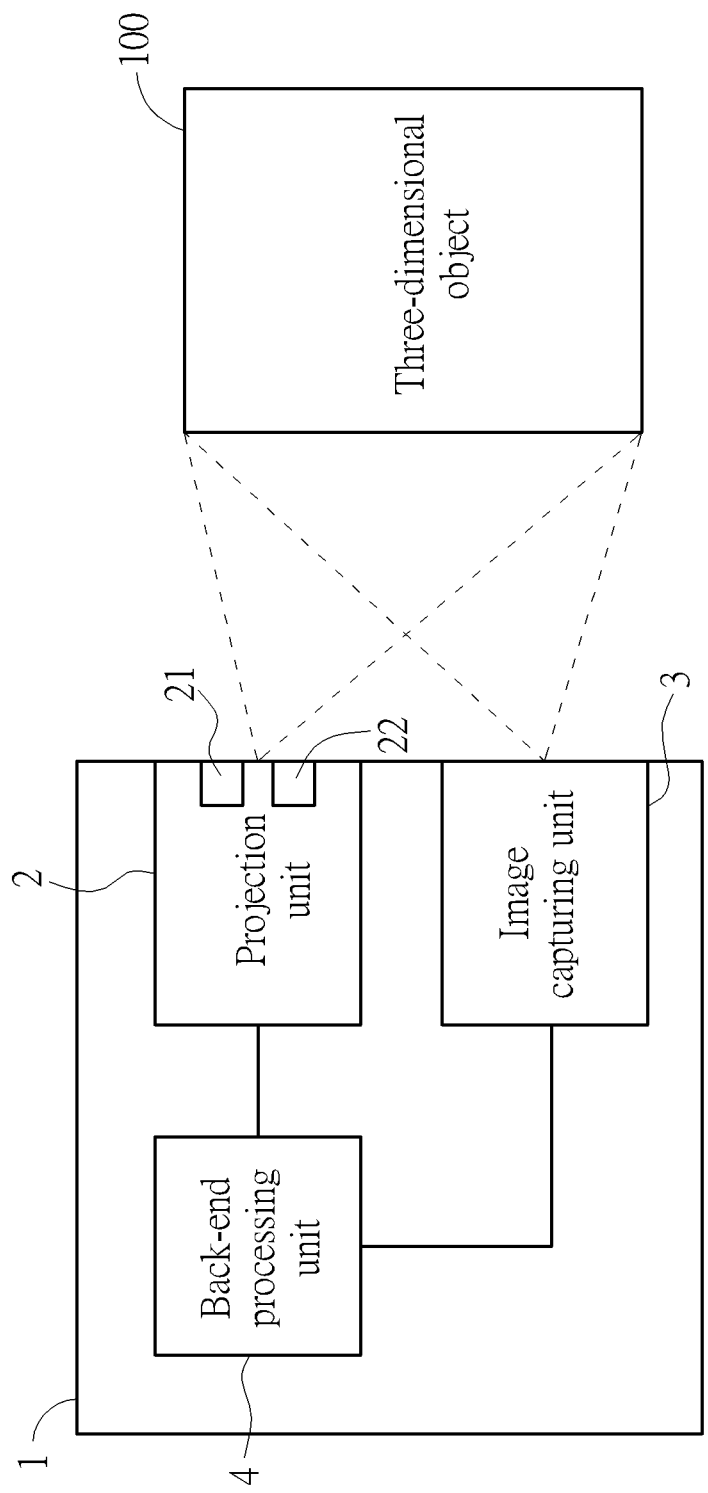
FIG. 1 is a functional block diagram illustrating a three-dimensional object scanning device according to an embodiment of the invention.

Referring to FIG. 1, FIG. 1 is a functional block diagram illustrating a three-dimensional object scanning device according to an embodiment of the invention. The three-dimensional object scanning device 1 is used to project structured lights to scan a three-dimensional object 100, capture an image of the structured lights on the three-dimensional object 100, and perform comparison and calculation, so as to obtain the size and shape of the three-dimensional object 100. In an embodiment, the three-dimensional object scanning device 1 of the invention is an intraoral scanner (IOS) for scanning the teeth or gum in an oral cavity, so as to construct a three-dimensional model of the teeth or gum. The three-dimensional object scanning device 1 comprises a projection unit 2, an image capturing unit 3, and a back-end processing unit 4. The projection unit 2 is configured to project a predetermined image (i.e. structure light with specific pattern) to a surface of the three-dimensional object 100 and the predetermined image is distorted and deformed by the surface of the three-dimensional object 100 to forma constructed image. The image capturing unit 3 captures the constructed image formed on the surface of the three-dimensional object 100 and then the back-end processing unit constructs a three-dimensional model of the three-dimensional object 100 according to the comparison between the constructed image and the predetermined image.

The projection unit 2 of the invention comprises a first monochrome light source 21 and a second monochrome light source 22. For the three-dimensional object scanning device 1 served as an intraoral scanner, in order to get used to specific environment in the oral cavity and reduce interference of reflective light, the invention may preferably use a blue light source to be the first monochrome light source 21 and use a green light source to be the second monochrome light source 22. In a preferred embodiment, the projection unit 2 may only comprise the blue light source and the green light source (i.e. without disposing a red light source), so as to reduce interference of white and/or red light from the three-dimensional object 100 and further optimize size, efficiency, power consumption, cost, and so on.

Besides using the blue light source and the green light source to be main light sources for projecting structured lights to avoid interference of color light and reduce reflective light on the three-dimensional object 100, the invention may further perform spatial coding for the structured light pattern projected by the projection unit 2. Accordingly, each partial region of each pattern will have specific coding information, such that it is more beneficial to the comparison between the constructed image and the predetermined image. Furthermore, the manner of using structured lights to perform scan may include multi-shots and single-shot. The invention provides some patterns with spatial coding to be the structured light pattern for constructing a three-dimensional model in multi-shots and single-shot.

Figure 2:
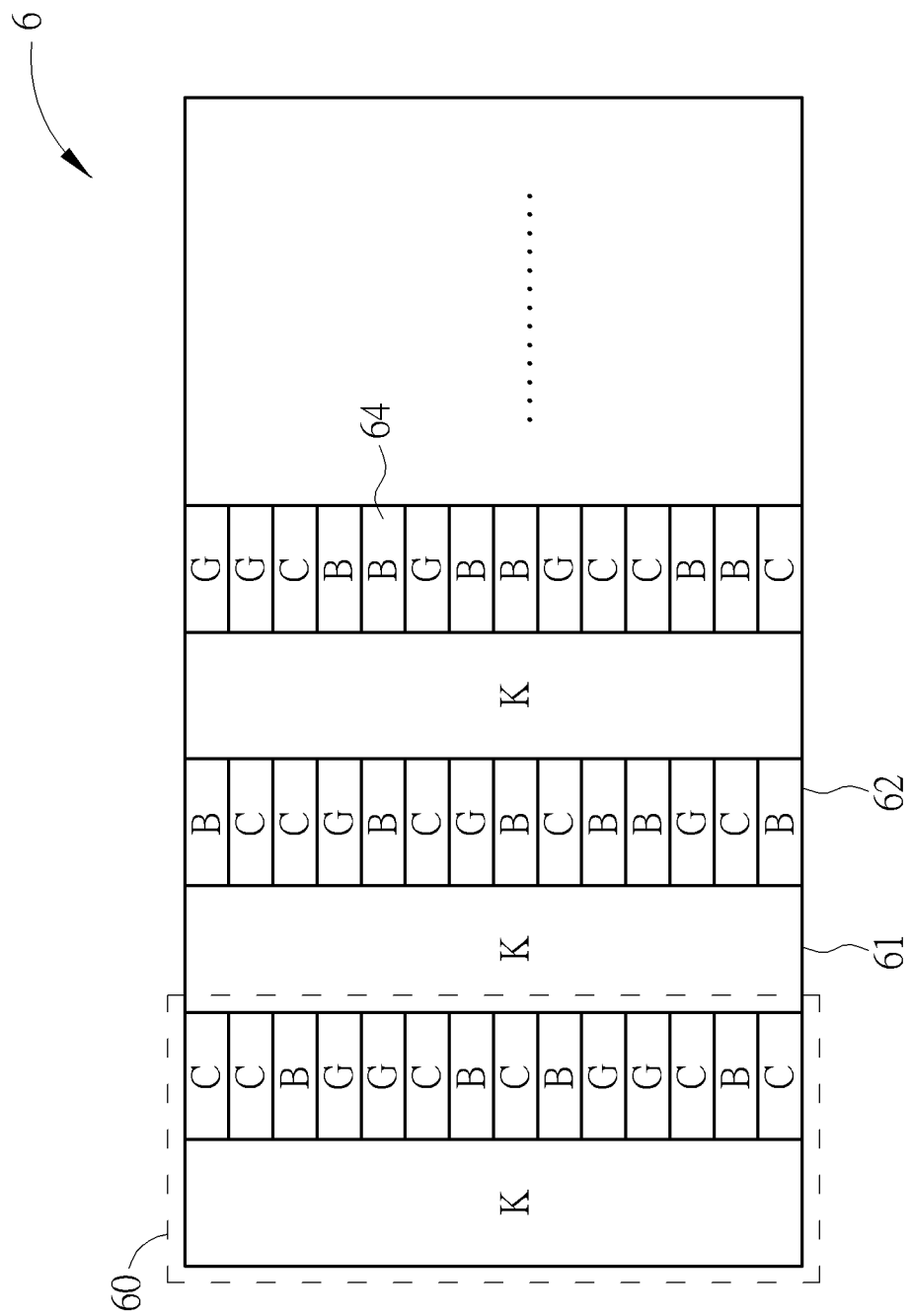
FIG. 2 is a schematic diagram illustrating a predetermined image of the structured lights projected by the three-dimensional object scanning device according to a first embodiment of the invention.

Referring to FIG. 2, FIG. 2 is a schematic diagram illustrating a predetermined image of the structured lights projected by the three-dimensional object scanning device according to a first embodiment of the invention. The predetermined image 6 comprises a plurality of default patterns 60 and each of the default patterns 60 comprises a first group of color blocks 61 and a second group of color blocks 62. In this embodiment, the default patterns 60 are arranged side by side to form the predetermined image 6, such that the first groups of color blocks 61 and the second groups of color blocks 62 of the default patterns 60 are interlaced with each other. Accordingly, the predetermined image 6 of the first embodiment is a structured light with striped pattern. The first group of color blocks 61 and the second group of color blocks 62 consist of a plurality of color blocks 64 with different colors. In each default pattern 60 of the predetermined image 6 with striped pattern, the first group of color blocks 61 is black block K and the second group of color blocks 62 comprises two or three different color blocks. For example, in the first embodiment, the second group of color blocks 62 comprises two or three color blocks 64 including blue blocks B, green blocks G, and cyan blocks C, wherein the blue blocks B are generated by projection of the first monochrome light source 21 of blue, the green blocks G are generated by projection of the second monochrome light source 22 of green, and the cyan blocks C are generated by projection of both of the first monochrome light source 21 and the second monochrome light source 22. The arrangements of the color blocks 64 in the second groups of color blocks 62 of the default patterns 60 are different from each other. Accordingly, for the predetermined image 6, the default patterns 60 are different from each other. That is to say, each of the default patterns 60 has specific coding information. When the predetermined image 6 is projected to the three-dimensional object 100 and forms a constructed image corresponding to the predetermined image 6, the image capturing unit 3 captures the constructed image and positions the corresponding location rapidly by means of pattern content obtained from partial region, such that the back-end processing unit 4 can construct a three-dimensional model of the three-dimensional object 100 according to the constructed image and the predetermined image 6.

Figure 3:
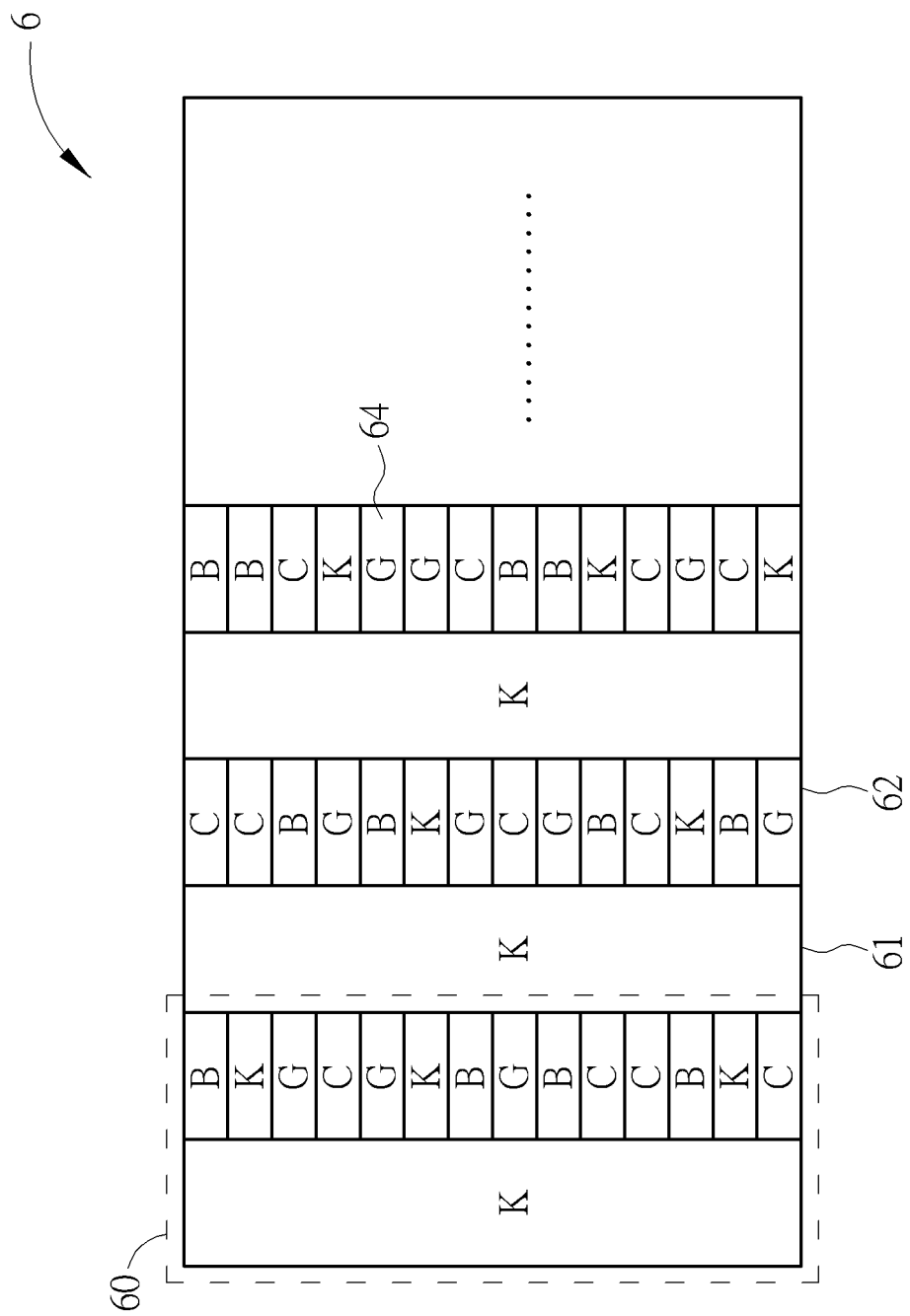
FIG. 3 is a schematic diagram illustrating a predetermined image of the structured lights projected by the three-dimensional object scanning device according to a second embodiment of the invention.

Referring to FIG. 3, FIG. 3 is a schematic diagram illustrating a predetermined image of the structured lights projected by the three-dimensional object scanning device according to a second embodiment of the invention. Compared to the first embodiment shown in FIG. 2, the second group of color blocks 62 may also comprise black blocks K. That is to say, the second group of color blocks 62 of each default pattern 60 comprises at least two and at most four different color blocks 64 including blue blocks B, green blocks G, cyan blocks C, and black blocks K, wherein each second group of color blocks 62 is formed by arranging at least two and at most four different color blocks 64 in a manner different from other second groups of color blocks 62. It should be noted that the images of the structured lights with striped pattern of black and specific color shown in FIGS. 2 and 3 may be preferably applied to scan a three-dimensional object by multi-shots, but is not so limited.

Figure 4:
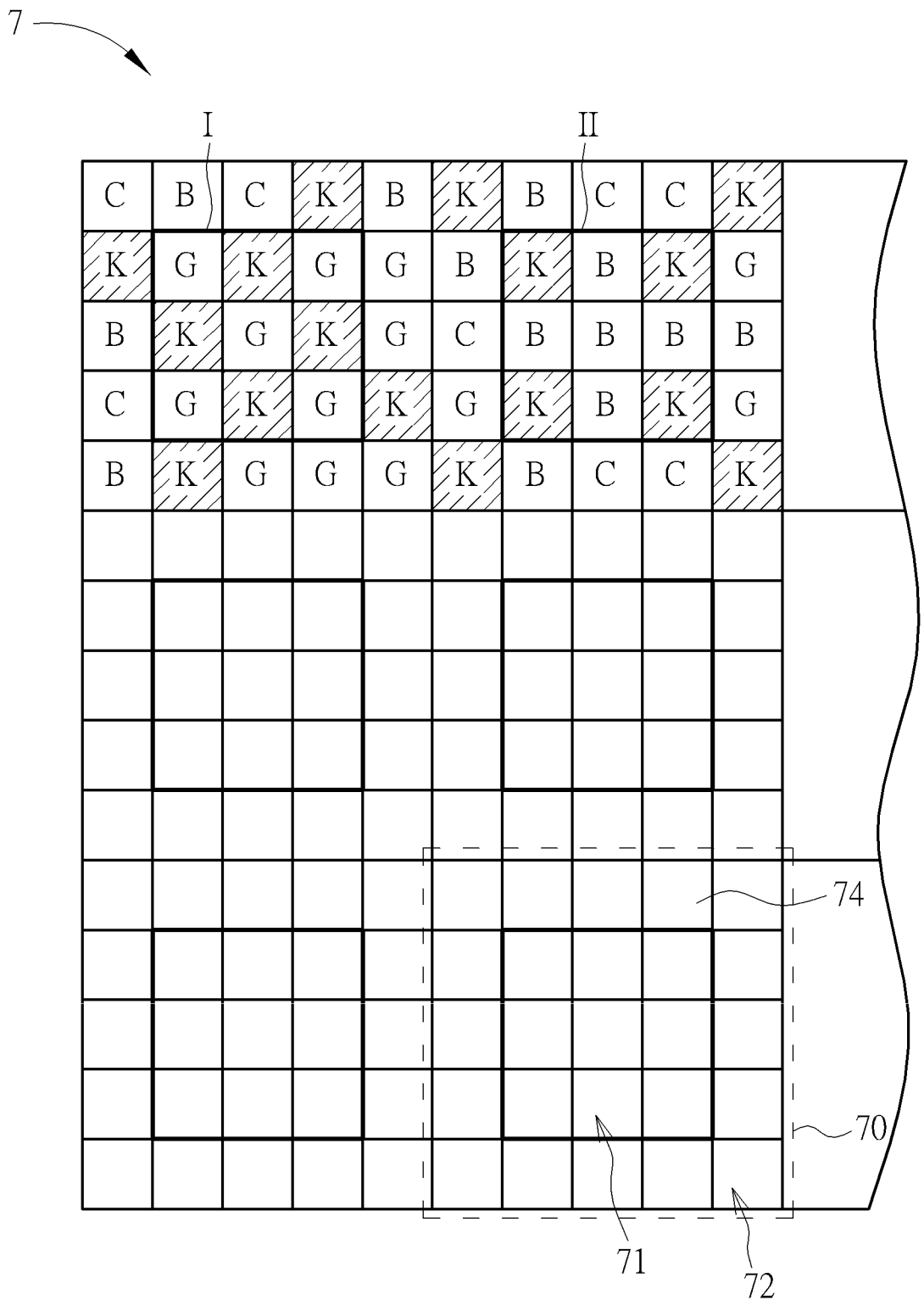
FIG. 4 is a schematic diagram illustrating a predetermined image of the structured lights projected by the three-dimensional object scanning device according to a third embodiment of the invention.

Referring to FIG. 4, FIG. 4 is a schematic diagram illustrating a predetermined image of the structured lights projected by the three-dimensional object scanning device according to a third embodiment of the invention. The predetermined image 7 comprises a plurality of default patterns 70 and each of the default patterns 70 comprises a first group of color blocks 71 and a second group of color blocks 72. In this embodiment, the default patterns 70 are arranged in a checkerboard manner to form the predetermined image 7. Accordingly, the predetermined image 7 of the third embodiment is a structured light consisting of a plurality of color block regions. Each of the default patterns 70 is a square pattern comprising n*n color blocks 74. In the third embodiment of FIG. 4, each of the default patterns 70 comprises 5*5 color blocks 74. In another embodiment, n may be a positive integer larger than 5. The first group of color blocks 71 and the second group of color blocks 72 comprise a plurality of color blocks 74 with different colors, wherein the first group of color blocks 71 of each default pattern 70 comprises 3*3 color blocks 74 in a center of the default pattern 70 and the second group of color blocks 72 comprises other color blocks 74 of the default pattern 70 (i.e. the color blocks 74 surrounding the first group of color blocks 71), wherein the first group of color blocks 71 comprises two different color blocks 74 and the second group of color blocks 72 comprises at least two and at most four different color blocks 74.

In the third embodiment, the first group of color blocks 71 may have a first pattern type I and a second pattern type II. As shown in FIG. 4, four edge blocks of the first group of color blocks 71 of the first pattern type I (i.e. the color blocks 74 located at four edges of the 3*3 color blocks 74 except the corner blocks) are black blocks K, and other color blocks 74 of the first group of color blocks 71 may be blue blocks B, green blocks G, or cyan blocks C and have identical color (e.g. the green blocks G shown in the figure). On the contrary, four corner blocks of the first group of color blocks 71 of the second pattern type II (i.e. the color blocks 74 located at four corners of the 3*3 color blocks 74) are black blocks K, and other color blocks 74 of the first group of color blocks 71 may be blue blocks B, green blocks G, or cyan blocks C and have identical color (e.g. the blue blocks B shown in the figure). As to the second group of color blocks 72, the second group of color blocks 72 comprises at least two and at most four different color blocks 74 including blue blocks B, green blocks G, cyan blocks C, and black blocks K, and the arrangements of the color blocks 74 in the second groups of color blocks 72 of the default patterns 70 are different from each other.

For the predetermined image 7, the default patterns 70 are different from each other. That is to say, each of the default patterns 70 has specific coding information. For example, the coding manner of the third embodiment may perform comparison and determination rapidly through at least three steps. When the image capturing unit 3 captures the constructed image (e.g. the deformed image generated by projecting at least partial predetermined image 7 to the three-dimensional object 100) corresponding to at least a part of the predetermined image 7, the back-end processing unit 4 determines that the constructed image corresponds to a specific default pattern 70 of the predetermined image 7. First, the back-end processing unit 4 determines that the first group of color blocks 71 at the inner ring of the constructed image is the first pattern type I or the second pattern type II. Then, the back-end processing unit 4 determines that the non-black blocks of the first group of color blocks 71 are blue blocks B, green blocks G, or cyan blocks C. In this way, the default patterns 70 of the predetermined image 7 arranged in a checkerboard manner will be filtered to ⅙ default patterns 70. Then, the back-end processing unit 4 compares the second group of color blocks 72 at the middle and outer rings of the default patterns 70, such that the back-end processing unit 4 can position the location of the constructed image rapidly by the content of the constructed image obtained from partial region on the three-dimensional object 100.

It should be noted that the second group of color blocks 72 of the third embodiment may comprise at least two and at most four different color blocks 74 including blue blocks B, green blocks G, cyan blocks C, and black blocks K (as shown in FIG. 4) or, alternatively, comprise at least two and at most three different color blocks 74 including blue blocks B, green blocks G, and cyan blocks C without black blocks K. The image of the structured lights shown in FIG. 4 may be preferably applied to scan a three-dimensional object by single-shot, but is not so limited.

Figure 5:
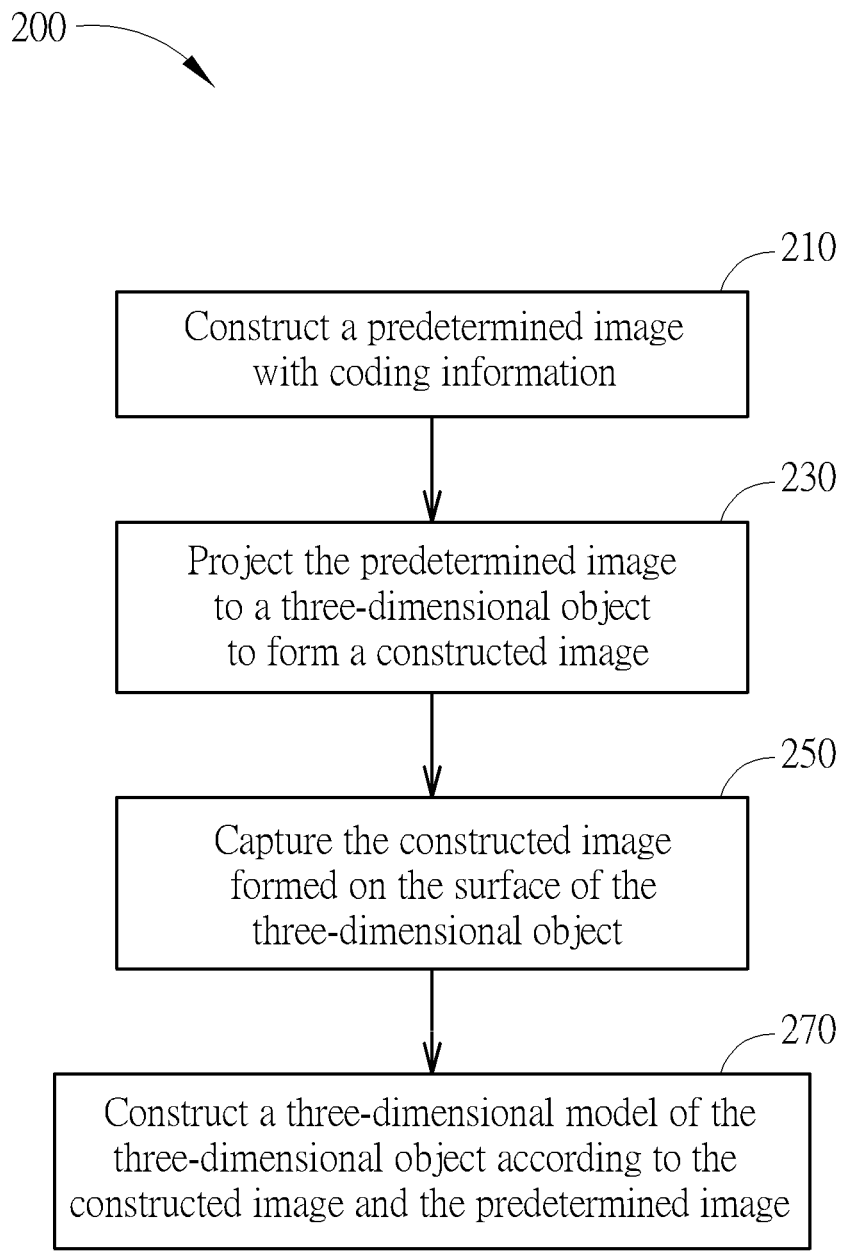
FIG. 5 is a flowchart illustrating a method for scanning a three-dimensional object using structured lights by the three-dimensional object scanning device of the invention.

Referring to FIG. 5, FIG. 5 is a flowchart illustrating a method for scanning a three-dimensional object using structured lights by the three-dimensional object scanning device of the invention. The method 200 comprises steps of:

Step 210: Construct a predetermined image with coding information;

Step 230: The projection unit projects the predetermined image to a three-dimensional object to form a constructed image on a surface of the three-dimensional object;

Step 250: The image capturing unit captures the constructed image formed on the surface of the three-dimensional object;

Step 270: The back-end processing unit constructs a three-dimensional model of the three-dimensional object according to the constructed image and the predetermined image.

In step 210, the manner of constructing the predetermined image is mentioned in the above, so it will not be depicted herein again. In step 230, the projection unit projects blue blocks of the predetermined image by the first monochrome light source, projects green blocks of the predetermined image by the second monochrome light source, and projects cyan blocks of the predetermined image by both of the first monochrome light source and the second monochrome light source, wherein black blocks of the predetermined image are formed without projecting any lights.

The invention provides a three-dimensional object scanning device using structured lights and method using the same. A combination of specific monochrome light sources is used to construct the content of the structured lights to form a predetermined image, which is projected to the three-dimensional object such as an intraoral object. The combination of blue and green lights effectively eliminates reflective interference of the red or white environment within the intraoral space. Default patterns of the predetermined image are distinguished from one another by using well designed arrangement of color blocks so that specific coding information of location may be embedded and exploited.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A three-dimensional object scanning device using structured lights, comprising:
a projector comprising a first monochrome light source and a second monochrome light source, the projector projecting a predetermined image to a three-dimensional object, so as to form a constructed image on a surface of the three-dimensional object, the predetermined image comprising a plurality of default patterns, each of the default patterns comprising:
a first group of color blocks comprising at most two different color blocks; and
a second group of color blocks comprising at least two and at most four different color blocks; and
an image capturer capturing the constructed image formed on the surface of the three-dimensional object;
wherein the default patterns are square patterns and each of which comprises n*n color blocks, the n*n color blocks are arranged in a checkerboard manner to form the predetermined image, n is a positive integer larger than or equal to 5, the first group of color blocks of each default pattern comprises 3*3 color blocks in a center of the default pattern, the second group of color blocks comprises a plurality of color blocks surrounding the first group of color blocks, the first group of color blocks of each default pattern has a first pattern type and a second pattern type, four edge blocks of the first pattern type are black blocks, four corner blocks of the second pattern type are black blocks, other non-black blocks in the first group of color blocks with the first pattern type are blue blocks, green blocks, or cyan blocks and have identical color, other non-black blocks in the first group of color blocks with the second pattern type are blue blocks, green blocks, or cyan blocks and have identical color, the blue blocks are generated by projection of the first monochrome light source, the green blocks are generated by projection of the second monochrome light source, and the cyan blocks are generated by projection of both of the first monochrome light source and the second monochrome light source.

2. The three-dimensional object scanning device of claim 1, wherein each second group of color blocks is formed by arranging at least two and at most four different color blocks in a manner different from other second groups of color blocks and surrounding the first group of color blocks.

3. The three-dimensional object scanning device of claim 1, wherein the first monochrome light source is a blue light source, the second monochrome light source is a green light source, and the projector only comprises the blue light source and the green light source.

4. The three-dimensional object scanning device of claim 1, further comprising a back-end processor constructs a three-dimensional model of the three-dimensional object according to the constructed image and the predetermined image.

5. The three-dimensional object scanning device of claim 4, wherein the three-dimensional object is a tooth and the three-dimensional object scanning device is an intraoral scanner.

6. A method for scanning a three-dimensional object using structured lights, a three-dimensional object scanning device comprising a projector and an image capturer, the projector comprising a first monochrome light source and a second monochrome light source, the method comprising steps of:
the projector projecting a predetermined image to a three-dimensional object, so as to form a constructed image on a surface of the three-dimensional object, the predetermined image comprising a plurality of default patterns, each of the default patterns comprising a first group of color blocks and a second group of color blocks, the first group of color blocks comprising at most two different color blocks, the second group of color blocks comprising at least two and at most four different color blocks; and the unit capturer capturing the constructed image formed on the surface of the three-dimensional object;

wherein the projector projects a square pattern comprising n*n color blocks to form each default pattern and the n*n color blocks are arranged in a checkerboard manner to form the predetermined image, n is a positive integer larger than or equal to 5, the first group of color blocks of each default pattern projected by the projector comprises 3*3 color blocks in a center of the default pattern, the second group of color blocks projected by the projector comprises a plurality of color blocks surrounding the first group of color blocks, the projector projects each default pattern, the first group of color blocks of each default pattern has a first pattern type and a second pattern type, four edge blocks of the first pattern type are black blocks, four corner blocks of the second pattern type are black blocks, blue blocks in the first group of color blocks and the second group of color blocks are generated by projection of the first monochrome light source, green blocks in the first group of color blocks and the second group of color blocks are generated by projection of the second monochrome light source, cyan blocks in the first group of color blocks and the second group of color blocks are generated by projection of both of the first monochrome light source and the second monochrome light source, the projector projects blue blocks, green blocks, or cyan blocks to other non-black blocks in the first group of color blocks with the first pattern type, and the projector projects blue blocks, green blocks, or cyan blocks to other non-black blocks in the first group of color blocks with the second pattern type.

7. The method of claim 6, wherein the projector forms and projects each second group of color blocks by arranging at least two and at most four different color blocks in a manner different from other second groups of color blocks and surrounding the first group of color blocks.

8. The method of claim 6, further comprising step of:
using a blue light source to be the first monochrome light source and using a green light source to be the second monochrome light source, wherein the projector only comprises the blue light source and the green light source.

9. The method of claim 6, wherein the three-dimensional object scanning device further comprises a back-end processor and the method further comprises step of:
the back-end processor constructing a three-dimensional model of the three-dimensional object according to the constructed image and the predetermined image.

* * * * *